United States Patent [19]

DeCant, Jr. et al.

[11] 4,443,218
[45] Apr. 17, 1984

[54] PROGRAMMABLE IMPLANTABLE INFUSATE PUMP

[75] Inventors: Leonard J. DeCant, Jr., Allston; Samir F. Idriss, Arlington, both of Mass.

[73] Assignee: Infusaid Corporation, Norwood, Mass.

[21] Appl. No.: 416,282

[22] Filed: Sep. 9, 1982

[51] Int. Cl.³ .............................................. A61M 5/14
[52] U.S. Cl. ............................. 604/67; 128/DIG. 12; 128/DIG. 13
[58] Field of Search ............................. 604/891, 67; 251/61–61.5; 92/3, 9, 34–35, 37–39, 43; 222/207; 417/472–473; 128/903, DIG. 12, DIG. 13; 72/54

[56] References Cited

U.S. PATENT DOCUMENTS

| | | | |
|---|---|---|---|
| 3,450,153 | 6/1969 | Hildebrandt et al. | 128/DIG. 13 |
| 3,529,908 | 9/1970 | Smith | 92/43 |
| 3,731,681 | 5/1973 | Blackshear et al. | 604/141 |
| 3,936,028 | 2/1976 | Norton et al. | 251/61.1 |
| 4,047,851 | 9/1977 | Bender | 417/472 |
| 4,171,218 | 10/1979 | Hoshino et al. | 72/54 |
| 4,237,900 | 12/1980 | Schulman et al. | 128/903 |
| 4,274,444 | 6/1981 | Ruyak | 251/65 |
| 4,350,647 | 9/1982 | de la Cruz | 128/205.23 |
| 4,364,276 | 12/1982 | Shimazoe et al. | 73/706 |
| 4,376,523 | 3/1983 | Goyew | 251/61.1 |

*Primary Examiner*—William E. Kamm
*Assistant Examiner*—Steven Falk
*Attorney, Agent, or Firm*—Cesari and McKenna

[57] ABSTRACT

A programmable implantable infusion pump includes a housing containing a variable volume infusate chamber and variable volume control fluid pressure and displacement reservoirs. A conduit conducts infusate from the chamber exteriorly of the housing. A restricted fluid path exists between the two reservoirs which are filled with an incompressible control fluid. A loaded spring applies a constant force to the pressure reservoir causing fluid flow between the two reservoirs. The differential pressure across the flow restriction is sampled by a microprocessor which computes the fluid flow rate, that rate being proportional to the infusate flow rate from the chamber. When the fluid flow rate deviates from a programmed value, the processor issues an error command to a battery-driven motor which reloads the spring to reestablish the constant force on the pressure reservoir. The infusate flow rate may be changed automatically during the day in accordance with a programmed schedule and that schedule may be changed by reprogramming the processor using a telemetry receiver contained in the housing.

28 Claims, 5 Drawing Figures

U.S. Patent     Apr. 17, 1984     4,443,218
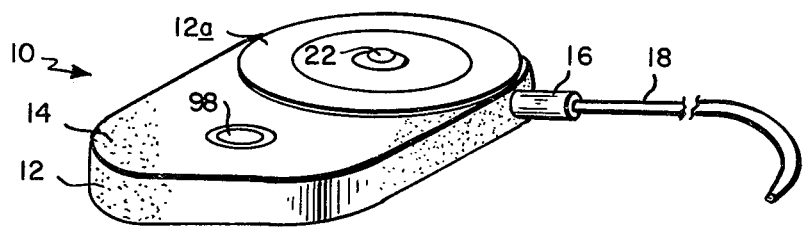
FIG.1
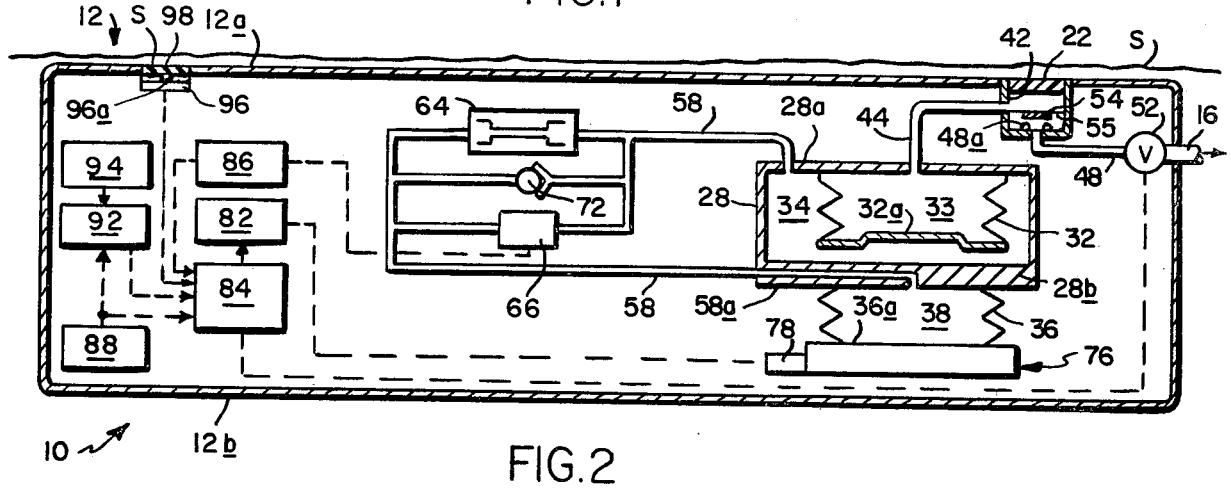
FIG.2
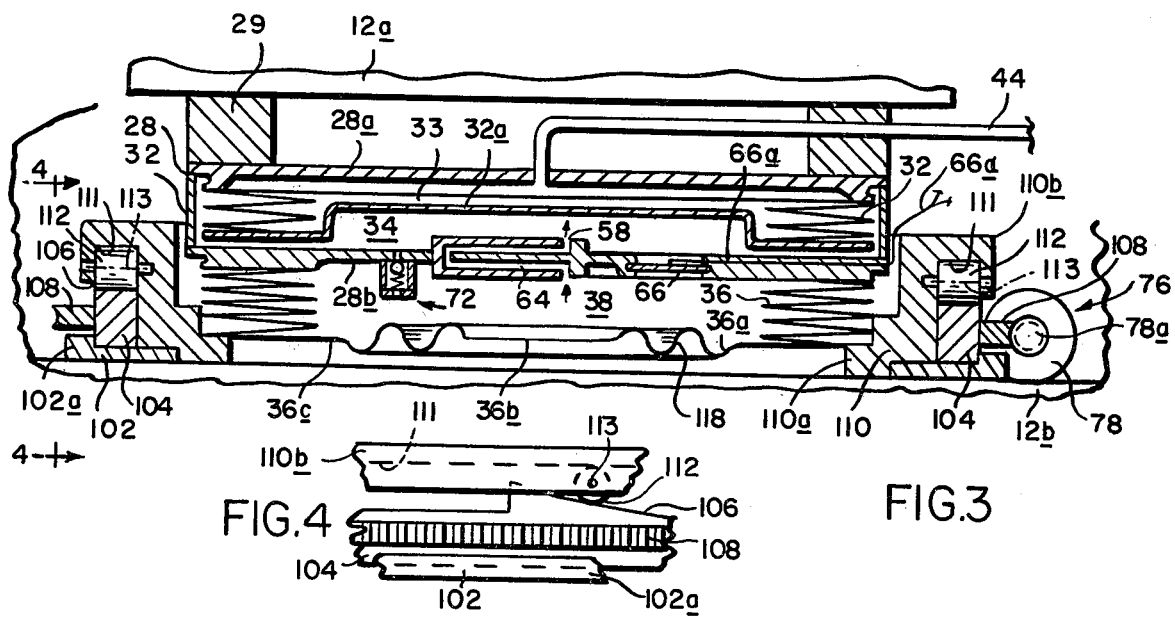
FIG.3
FIG.4
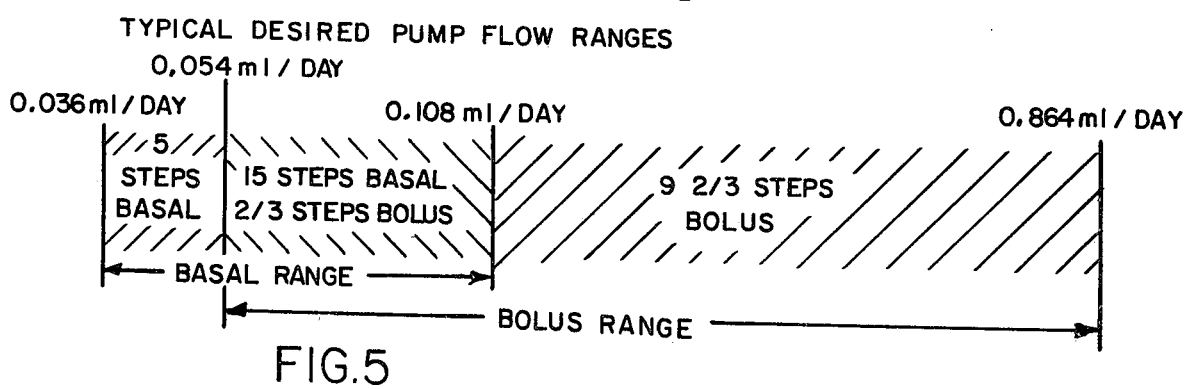
TYPICAL DESIRED PUMP FLOW RANGES
FIG.5

PROGRAMMABLE IMPLANTABLE INFUSATE PUMP

This invention relates to an implantable infusate pump. It relates more particularly to a pump of this type which automatically dispenses infusate to a patient at different flow rates depending upon the patient's requirements.

BACKGROUND OF THE INVENTION

In recent years, infusion apparatus has been developed which can be implanted in the body and remain there for a prolonged period. The apparatus can be refilled with infusate without having to remove the apparatus from the patient's body by injecting additional infusate through a penetrable septum in the apparatus wall located directly under the patient's skin. Examples of infusion apparatus of this general type are disclosed in U.S. Pat. Nos. 3,731,681 and 3,951,147.

In the treatment of some patients such as those afflicted with diabetes, the amount of medication such as insulin infused per unit of time should be adjusted at certain time intervals. This is because the requirements of the patient usually fluctuate during the day, such fluctuations being caused, for example, by the ingestion of food. Some prior implantable infusion apparatus provide this flexibility, examples being shown in U.S. Pat. Nos. 3,894,538 and 4,077,405.

It has also been proposed to program the daily administration of medication such as insulin. In such apparatus, the piston of an infusate injector is moved by a motor drive in accordance with said program in such a way that the desired daily dose is achieved while accounting for fluctuations in the patient's glucose level, temperature and the ambient pressure to which the patient is subjected. See U.S. Pat. No. 4,003,379 and the references cited therein.

The aforesaid implantable infusion pumps are, however, disadvantaged in one or another of the following respects. Some require an excessive number of mechanical components. This renders it impractical to manufacture such devices with the required small size to enable them to be implanted in the patient's body without undue discomfort to the patient. Some of the prior devices control infusate flow by means of flow restrictions or controllable valves. If the infusate is a type of fluid such as insulin whose molecules agglomerate when they are disturbed, the resultant squeezing of the infusate through such restrictions and valving damages the molecules and also causes clogging of those restricted passages.

Further, some of the conventional infusion devices of this general type have an excessive energy requirement either to develop the necessary pressure to dispense the infusate into the patient's body or to regulate that flow to provide the desired dosages. If the energy requirement is supplied by a battery, that battery has to be replaced or recharged relatively often, requiring, at the very least, penetration of the patient's skin, giving rise to the possibility of infection.

Some prior pumping apparatus of this type only dispense infusate to the patient intermittently or periodically which is disadvantageous in some instances. For example, tests have shown that diabetics should receive a basal dose of insulin which is continuous and the basal dose supplemented by so-called bolus doses at certain times of the day, such as at mealtimes. The difference in the basal and bolus flow rates may be several orders of magnitude and it is quite difficult to achieve proper flow control over that entire range of flow rates. The device disclosed in U.S. Pat. No. 4,140,122 does have the advantage of achieving a continuous dosing of infusate even at very small flow rates. However, that continuous feeding or injection of medication also requires a continuous generation of pressure and consequently a constantly higher requirement of input energy for the electrodes which control infusate flow. Furthermore, that requirement increases substantially when the rate of medication infeed increases.

In general, the prior comparable devices of which we are aware do not take into account all of the physiological concepts and clinical factors involved in the various therapies, particularly diabetes therapy, in connection with which such implantable devices are used. In general, such implantable infusion apparatus should have the ability to:

1. deliver infusate such as insulin at a wide range of bolus and basal flow rates, thereby accommodating the needs of the majority of the afflicted population;
2. tailor the infusate delivery scheme to individual patients without having to physically modify or alter the pump components;
3. control the required infusion rates to an extreme accuracy over long time intervals;
4. limit induced shear forces in the infusate, thereby maintaining its solution integrity;
5. allow external programming to permit patient/physician interaction; this allows the physician to (a) match the pump's flow rate parameters to each patient's requirement, (b) monitor the device for signs of past or impending failure, (c) retrieve information on past pump operations (e.g. average daily basal and bolus flow rates, total infusion delivery to date, etc.), and (d) allow the patient to set meal characteristics so that the bolus dose can be tailored for each meal instead of being set at a predetermined average dose level; and
6. exhibit long life capabilities on the order of ten years to be able to justify the cost of the device, the cost of the surgical implant and the medical risks undertaken by the patient. By the same token, the pump should also be adaptable to changes in long-term patient needs and changes in ambient operating conditions.

SUMMARY OF THE INVENTION

Accordingly, the present invention aims to provide implantable infusion apparatus which has all of the above abilities and is thus particularly adapted for use in connection with diabetes therapy.

Accordingly, it is an object of the present invention to provide implantable infusion apparatus which delivers a continuous flow of infusate to the patient at precisely controlled very low flow rates and at higher rates which may vary over a wide range.

Another object of the invention is to provide apparatus of this type which does not damage the infusate which it is dispensing and which is not prone to being clogged by that infusate.

A further object of the invention is to provide implantable infusion apparatus which can be programmed either externally or internally to vary the infusate dosage to the patient.

Still another object of the invention is to provide implantable infusion apparatus which delivers the programmed infusate dosage to the patient despite changes in patient temperature or in the atmospheric pressure to which the patient is subjected.

Another object of the invention is to provide apparatus of this type whose components can be contained in a relatively small package so that its implantation in a patient does not produce undue patient discomfort.

Yet another object of the invention is to provide implantable infusion apparatus having a minimum energy requirement so that it can remain operative in the patient for a prolonged period of time, i.e. on the order of three years or more.

A further object of the invention is to provide apparatus of this type which operates in a failsafe mode so that there is no danger of an excessive amount of infusate being delivered to the patient.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Generally in the present apparatus, the regulation of the infusate flow rate from an infusate dispensing chamber is achieved by regulating the rate of flow of a secondary more viscous control fluid from one reservoir to another through a fixed flow restriction. In this general sense, the present apparatus is similar to the dosing device disclosed in the aforementioned U.S. Pat. No. 4,140,122. In most other respects, however, it differs markedly from that prior device as will be seen presently.

The components of our apparatus are all contained within a relatively small, hermetically sealed housing made of a biocompatible material. These components include an insulin dispensing chamber, a control fluid displacement reservoir and a control fluid pressure reservoir, all preferably in the form of bellows capsules. Percutaneous access to the interior of the infusate chamber for refilling purposes is had by way of a penetrable septum in the housing wall which, when the apparatus is implanted, is located directly under the patient's skin. An unrestricted delivery tube leads from that same chamber to a catheter which is adapted to be located at an appropriate infusion site in the patient's body.

The fluid pressure reservoir is connected to the displacement reservoir by way of a fluid path including a flow restriction having known flow characteristics and dimensions. The two reservoirs and the path between them is filled with a substantially incompressible control fluid having a relatively high viscosity, usually higher than the infusate being dispensed by the apparatus. A differential pressure sensor is connected in parallel with the restriction and that sensor is monitored by an electronic pressure monitoring circuit contained in the housing.

A control circuit controls the operation of a small battery-operated electric motor which, in turn, transmits energy to a mechanical variable pressure source. That source applies pressure to the infusate chamber and/or the fluid pressure reservoir. The flow restriction, the pressure sensor and the electric motor together with its motor control circuit constitute a feedback loop which enables close control over infusate flow to be maintained by monitoring the pressure drop across the flow restriction.

Activation of the electric motor by the motor control circuit causes the mechanical variable pressure source to apply a collapsing force to the fluid pressure reservoir. This force develops a pressure differential across the restriction which, in turn, forces fluid from the fluid pressure reservoir to the displacement reservoir. The transducer monitors that pressure differential resulting in an application of an electrical output from the pressure monitoring circuit to a microprocessor contained in the housing. The processor thereupon calculates the volumetric flow rate of the control fluid between the two reservoirs. The flow rate of the infusate is directly proportional to the flow rate of the control fluid. Consequently, after calculating the control fluid flow rate, the microprocessor module determines the infusate flow rate.

By the use of an external transmitter, various desired infusate flow rates may be transmitted telemetrically to an antenna on a receiver located in the apparatus housing and that data is stored in the microprocessor. A comparison of those values with the value obtained by monitoring the control fluid flow rate as aforesaid determines whether or not the proper infusate flow rate control has been established at any given time. If that flow rate is not the desired one, indicating that the fluid pressure in the pressure reservoir is not correct, the motor is activated to cause the mechanical variable pressure source to reset to establish a pressure in the pressure reservoir that produces the desired infusate flow rate from the chamber. This process of resetting the pressure on the control fluid, monitoring the control fluid pressure differential and comparing the calculated control fluid flow rate to the one desired is repeated at appropriate sampling intervals until the proper infusate flow rate is obtained. From that point on, the pressure sensor is monitored by the pressure monitoring circuit at predetermined intervals and the motor activated only when that pressure differential deviates from a preset error limit.

The mechanical variable pressure source is not simply a rigid power transmission link between the motor and the fluid pressure reservoir. If this were the case, the motor would have to be a variable force electromechanical actuator such as is used in some prior implantable infusate pumps of this general type. Accordingly, that method of activation would have to be energy-intensive in order to continually maintain the required infusate pressure. Most probably also, it would be energy-inefficient due to the inherent efficiency limits of such electrical-to-mechanical power conversion devices. To avoid the aforesaid problems, the mechanical variable pressure source in the present apparatus transmits force through an elastic member such as a spring which is loaded intermittently by the electric motor so as to store constant force energy in the spring.

In other words, the spring is flexed to whatever force level is necessary to establish the desired pressure differential across the restriction that achieves the desired infusate flow rate. By tracking the movement of the fluid pressure reservoir and thereby maintaining more or less the same flexure of the spring, the apparatus establishes a constant force on that reservoir and therefore a constant infusate pressure on, and flow rate from, the infusate chamber. In other words, the motor applies potential energy to the spring which, in turn, is transformed to nearly constant pressure work on the infusate chamber at a much higher efficiency than can be accomplished by a direct drive between the motor and that chamber.

The mechanical variable pressure source is preferably reversible so that the infusate chamber can be refilled by subcutaneous injection through the septum which seals the inlet to the infusate chamber. This reversal can be achieved by employing a reversible DC motor and programming the microprocessor to reverse the polarity of the battery voltage applied to that motor. Alternatively, the drive motor can be connected to the mechanical variable pressure source by way of a clutch or similar linkage which permits the infusate chamber and fluid pressure reservoir to expand under the pressure of the fresh infusate being injected into the infusate chamber through the septum. During refilling, a check valve in the fluid path between the infusate chamber inlet and outlet closes to prevent infusate flow directly from the inlet to the outlet.

The apparatus also includes a valved bypass in parallel with the flow restriction between the two fluid pressure reservoirs so that, during the refilling operation, the restriction is shortcircuited, thereby permitting the refilling process to take place relatively quickly and at a relatively low refill needle pressure, thereby reducing stress on the components of the apparatus.

With apparatus such as this used to control a life-dependent physiological event, safety is of the highest priority. Accordingly, the present apparatus includes an electrically controlled, failsafe valve in the outlet line from the infusate chamber. The microprocessor in the apparatus employs the pressure differential signal developed by the transducer for safety monitoring purposes. If that differential deviates from the desired value for a predetermined time interval, the microprocessor issues a command signal which automatically closes that valve, thereby discontinuing infusate flow to the patient. That valve can also be designed to be actuated externally, using a magnet for example. Accordingly, if there were catastrophic failures of both the electronic and mechanical components of the apparatus, the patient would still be able to discontinue insulin flow manually.

Thus the present apparatus possesses all of the requirements for a successful implantable infusate pump enumerated above. The pump is able to be programmed externally and noninvasively by a physician, allowing its output to be matched to patient infusate demands. Further, continuous monitoring of the pump's operation and its inherent data storage allows the physician to determine certain parameters such as the quantity of insulin delivered to the patient during a particular operating cycle. Likewise, the apparatus permits a certain amount of patient control. For example, in the case of insulin infusate, it permits the patient to initiate the higher bolus mealtime rate and to change that rate according to certain requirements, for example, to match his caloric intake during each meal.

Also, the continuous flow control capability of the present device allows a finer resolution of control over infusate flow than is possible with the discreet volume injection devices found in the prior art. There are definite clinical indications in diabetic therapy that such continuous flow therapy provides more precise blood sugar management and less physiological damage than devices which provide "digital" control over infusate flow.

Further, by placing a flow restriction in the control fluid circuit and using that circuit to limit the infusate flow rate, shear forces on the infusate are greatly reduced. Therefore, the infusate solution integrity is maintained, permitting use of higher concentrations which, in turn, permit reduction of the pump size.

Other advantages of the present apparatus include (1) greater dependence on electronic components which implies less dependence on mechanical components, thereby making the entire system smaller, yet more reliable; and (2) redundancy which can be built into the apparatus relatively economically since it is more cost efficient to design redundant electronic systems than mechanical systems.

Also by using a secondary or control fluid to control infusate flow, whose viscosity is large compared to the infusate, the flow of that control fluid can be controlled accurately without any need to control the infusate viscosity. This permits the clinical use of a variety of infusate concentrations, formulations and brands. Further, the control fluid can be chosen such that its viscosity-temperature coefficient is much lower than that of the infusate or the fluid propellant used in some prior pumps of this general type. This makes the present pump less sensitive to temperature variations.

Finally, because the apparatus is pressure regulated and monitored by way of the control fluid, variations in ambient pressure can be accounted for during its operation.

BRIEF DESCRIPTION OF THE DRAWING

For a fuller understanding of the nature and objects of the invention, reference should be had to the following detailed description, taken in connection with the accompanying drawing, in which:

FIG. 1 is a perspective view of programmable implantable infusate apparatus embodying the principles of this invention;

FIG. 2 is a schematic view showing the components of the FIG. 1 apparatus in greater detail;

FIG. 3 is a sectional view on a larger scale showing certain mechanical components of the FIG. 1 apparatus in still greater detail;

FIG. 4 is a fragmentary sectional view illustrating the operation of the FIG. 1 apparatus; and FIG. 5 is a diagrammatic view showing typical flow rates of the FIG. 1 apparatus.

DESCRIPTION OF THE PREFERRED EMBODIMENT

Referring to FIG. 1 of the drawing, the subject apparatus is indicated generally at 10. It comprises a relatively small compact housing 12 made of a suitable biocompatible material such as titanium metal. Preferably, the housing is coated with a plastic material 14 such as silicone rubber which is also compatible with the human system. The illustrated apparatus is on the order of ⅝ inch thick and has an outside diameter of about 3⅜ inches.

In use, the apparatus 10 is implanted in a patient's subdermal cavity created in the upper chest and tied to the chest muscles. Apparatus 10 delivers infusate to the patient by way of a flexible outlet tube 16 to a silicone rubber catheter 18 which is inserted into an appropriate infusion site in the patient's body, say, the superior vena cava by way of the upper subclavian vein. A penetrable septum 22 is situated in the upper wall 12a of housing 12. When the apparatus is properly implanted, the septum 22 is located just under the skin so that the apparatus 10 can be refilled periodically by injecting infusate percutaneously through the septum.

Referring now to FIGS. 2 and 3, positioned inside housing 12 is a small container 28 mounted by a ring 29 to the housing top wall 12a. The container top wall 28a functions as a header for a collapsible infusate container, preferably in the form of a metal bellows capsule 32. This bellows capsule has a closed end wall 32a and defines an infusate chamber 33 inside the bellows and a so-called displacement reservoir 34 inside container 28, but outside the bellows.

The container bottom wall 28b functions as a header for a second metal bellows capsule 36 located outside the container. Bellows capsule 36 has a closed end wall 36a and defines a fluid pressure reservoir 38.

Infusate is introduced into infusate chamber 33 by way of a refill chamber 42 which is connected to chamber 33 by a conduit 44. Chamber 42 communicates with an opening in the upper wall of housing 12 which is closed by the self-sealing septum 22. A second conduit 48 extends from the floor of chamber 42 via a normally open electrically actuated valve 52 to outlet tube 16 which passes through the housing 12 wall to catheter 18.

The end of tube 48 inside chamber 42 functions as a valve seat 48a. Mounted inside chamber 42 is a valve member 54 which is biased open by a helical spring 55 and is movable from that open position spaced from valve seat 48a to a position wherein it engages against seat 48a and prevents fluid flow through tube 48. The spring 55 is similar to the one depicted in copending application Ser. No. 376,686, filed May 10, 1982, entitled IMPLANTABLE MAGNETICALLY-ACTUATED VALVE owned by the assignee of the present application. Thus, normally fluid communication is established between the interior of bellows 32 and tube 16 by way of chamber 42. However, when bellows 32 is being refilled with infusate by projecting a needle through septum 22, the needle engages the valve member 54, thereby seating it against the valve seat 48a so that the incoming infusate cannot flow to tube 48, but rather is forced to flow into and to extend the bellows capsule 32.

If desired, appropriate filters may be included in tubes 44 and/or 48 to filter out any debris that might be entrained in the infusate injected into the bellows 32.

The displacement reservoir 34 inside container 28, but outside bellows 32 communicates with a tube 58. That tube extends through a passage 58a in container bottom wall 28b where it communicates with fluid pressure reservoir 38 inside bellows capsule 36. Tube 58 contains a flow restriction 64 for restricting fluid flow between reservoirs 34 and 38. Those two reservoirs, as well as the fluid path between them, are filled with a pressure-transmitting medium having a relatively high viscosity as compared with that of the infusate being dispensed and a low viscosity vs. temperature coefficient as compared with that of the infusate. One suitable pressure transmitting medium is dimethylpolysiloxane.

Connected in parallel with restriction 64 is a pressure transducer 66 which measures the pressure differential across the restriction and develops an electrical output in response to that pressure drop. Also connected in parallel with the restriction is a check valve 72 which is normally closed when fluid is flowing from reservoir 38 to reservoir 34 and is open when the pressure is in the reverse direction, thereby shortcircuiting the flow restriction 64.

Referring now to FIG. 2, a mechanical variable pressure source shown generally at 76 to be described in detail later acts between the bottom wall 12a of housing 12 and the bottom wall 36a of bellows 36 to control the extension of that bellows. The mechanical source is actuated by a small reversible DC electric motor or step motor 78 mounted inside housing 12. When the motor armature rotates in one direction, the mechanical source 76 exerts a force on bellows capsule 36 tending to collapse it. Resultantly, the viscous control fluid is forced from reservoir 38 through tube 58 containing restriction 64 to displacement reservoir 34. On the other hand, when the motor 78 armature rotates in the opposite direction, it actuates the mechanical source 76 so as to extend bellows capsule 36. This usually occurs only when the apparatus 10 is being refilled. In that event, fresh infusate is being injected into chamber 42 with the valve 54 therein closed. Therefore, the fresh infusate is drawn into infusate chamber 33 as bellows 32 extends. At the same time, the control fluid flows from displacement reservoir 34 to fluid pressure reservoir 38, bypassing the restriction 64 through the now open check valve 72.

Still referring to FIG. 2, the operation of motor 78 is governed by a motor control circuit 82 which responds to the output from a microprocessor 84. The main input to microprocessor 84 derives from a pressure monitoring circuit 86 which responds to the output from the pressure transducer 66. The control is such that the monitoring of the pressure differential across the restriction 64 by the transducer 66 and pressure monitoring circuit 86 and the control of the mechanical variable pressure source by the motor 78 and motor control circuit 82, all under the control of the microprocessor 84, take place in a feedback loop which establishes very close control over the flow of the control fluid from reservoir 38 to reservoir 34. That, in turn, permits close control over the flow of infusate from chamber 32 to catheter 18.

Power to the microprocessor 84 derives from an appropriate very small battery 88 such as a lithium iodine cell, positioned in housing 12. This type of battery is found to have a useful life of about three years or more.

The microprocessor 84 controls the basal and bolus rates of infusate flow from chamber 33 to the patient indirectly by controlling the flow of the control fluid from reservoir 38 to reservoir 34. The microprocessor can be preprogrammed to provide a selected infusate flow schedule.

Preferably, means are provided for reprogramming the microprocessor to change that schedule after the apparatus is implanted in the body without having to invade the body. In the illustrated embodiment, such means include a telemetry transceiver 92 having an antenna 94 inside housing 12. Telemetry signals from a programmer and transmitter (not shown) located outside the patient's body are picked up by antenna 94 and conditioned in the transceiver 92 which thereupon emits appropriate signals to the microprocessor to effect the program change.

Preferably also, means are provided for enabling the patient himself to change from one programmed flow rate to another at the appropriate times, say, mealtimes. In the illustrated apparatus, this control is achieved by a switch 96 mounted to the top wall 12a and connected electrically to microprocessor 84. The switch actuator 96a is accessible from without the housing by way of a resilient sealing membrane so that the switch can be actuated by pressure on the skin. If the pump is delivering the basal flow, depression of the switch causes the processor to follow the bolus flow program. A second depression causes the processor to switch back to the basal flow schedule, and so on. Such patient control over the flow selection can also be achieved by transmitting appropriate telemetry signals to receiver 92. The patient's external programmer might permit him to select a certain bolus flow within a certain safe range depending upon his estimated glucose intake. That programmer would not, however, enable the patient to reprogram the processor to change the prescribed flow rate ranges. Only the physician's programmer would be able to transmit the coded data to accomplish that.

The above described mechanical components of the apparatus 10 are all packaged very compactly inside housing 12 as shown in FIG. 3, the components there having the same identifying numerals as in the FIG. 2 schematic diagram. As seen in FIG. 3, the flow restriction 64, pressure transducer 66 and check valve 72 are all mounted directly in the container wall 28b. The fixed flow restriction can be, for example, a long length of capillary tubing communicating between reservoirs 38 and 34 or a meandering passage extending through the wall 28b as shown. The check valve 72 can be a spring-loaded ball-type valve mounted in wall 28b. The pressure transducer 66 is preferably a piezo-resistive bender mounted in the chamber wall 28b. When the bender is flexed, its resistance changes correspondingly. That change is reflected on the leads 66a connected to the pressure monitoring circuit 86 (FIG. 2).

Referring to FIGS. 3 and 4, the mechanical variable pressure source 76 comprises a flat ring 102 which is mounted to the housing bottom wall 12b. The ring 102 is formed with a raised flange 102a extending around its periphery. Rotatably positioned on the radially outer segment of ring 102 against its flange 102a is a ring 104. The upper surface of ring 104 constitutes a cam. More particularly, it is formed with a series of, say, four wedge-shaped ramps 106 which are spaced apart around the upper surface of ring 104. The ring 104 is also formed with a gear 108 extending around its perimeter. That gear meshes with a worm 78a which is rotated by motor 78 mounted to the housing bottom wall 12b.

Also, slidably seated on the flat ring 102 is a stepped ring 110. The bottom step 110a of that ring extends down inside ring 102 and engages under the radially outer margin 36c of bellows bottom wall 36a. If desired, it may be secured there by some suitable means. Ring 110 is further stepped so that it extends up inside ring 104 outboard of container 28. The upper edge of the ring terminates in a radially outwardly extending step or flange 110b which overlies ring 104 and the ramps 106 formed thereon.

A channel 111 is formed in the underside of ring flange 110b. Positioned in the channel is a series of rollers 112 rotatively mounted on axles 113 extending through the opposite walls of the channel 111. The rollers 112 are disposed opposite the ramps 106 on ring 104 and roll on those ramps. Thus, when the ring 104 is rotated in one direction by motor 78, ring 110 is cammed up away from the housing bottom wall 12b thereby collapsing bellows 36. Conversely, when ring 104 is rotated in the opposite direction by the motor, the ring 110 is free to move downward toward wall 12b, thereby to extend the bellows 36.

Still referring to FIG. 3, the bottom wall 36a of bellows 36 is formed as a spring. More particularly, that bottom wall is formed with ripples 118 so that the radially inner portion 36b of that bottom wall is flexible and resilient with respect to the radially outer portion 36c supported on ring 110.

During normal operation of the apparatus 10, the chamber 33 is filled with infusate, while the reservoirs 34 and 38 and the path between them are filled with the more viscous control fluid. The strain gauge pressure sensor 66 senses the pressure differential between the reservoirs 34 and 38 and applies that reading via the pressure monitoring circuit 86 to the microprocessor 84. The processor processes that information and compares it with the data programmed into the microprocessor 84. If that pressure drop is less than it should be, indicating that the control fluid pressure in reservoir 38 is too low, the processor issues a command to the motor control circuit 82. That circuit thereupon actuates or steps motor 78 in a direction that rotates ring 104 so as to urge the ring 110 in a direction that collapses the radially outer portion 36c of the bellows end wall 36a. Such movement of that bellows end wall portion increases the pressure on the control fluid in reservoir 38 with the result that the radially inner segment 36b of the bellows end wall 36a is flexed outwardly or downwardly as viewed in FIG. 3. Due to ripples 118, that segment 36b thereupon function as a relatively stiff spring so that it represents a constant force exerted on the bottom of reservoir 38. This force develops a pressure in the reservoir which, in turn, establishes a pressure differential across the fixed restriction 64 between the two reservoirs 34 and 38, forcing control fluid from the latter to the former reservoir. That control fluid flow is governed by the well-known equation for laminar flow of a Newtonian fluid through a narrow channel.

The pressure differential across restriction 64 is monitored by the strain gauge pressure transducer 66 so that a conditioned output is applied from the pressure monitoring circuit 86 to the microprocessor 84. The microprocessor, through a conventional programmed algorithm, processes that information to develop the control fluid volume flow rate from reservoir 38 to reservoir 34.

The flow rate of the infusate in chamber 33 is related to the flow rate of the control fluid in that the control fluid volume exactly displaces (in a one-to-one ratio) the infusate volume. Therefore, the microprocessor can calculate the actual infusate flow rate from chamber 33 to the catheter 18 (FIG. 1). The processor then compares this value with the programmed flow rate for the particular time of day or desired mode of operation, e.g. bolus flow during a meal. If the infusate flow rate is correct, the motor 78 remains deenergized and the control fluid in reservoir 38 remains at that pressure. On the other hand, if the pressure differential measured by the pressure sensor 66 is too low, indicating that the spring built into the bellows wall 36a is insufficiently stressed, the microprocessor 84 issues a command to motor 78 causing it to rotate the cam ring 104 so as to elevate ring 110 an increment. This reloads the spring built into the bellows to restore the desired constant pressure on the control fluid in reservoir 38. That, in turn, increases the flow through the restriction 64 to the displacement reservoir 34. The increased pressure drop across the restriction is sensed and applied to the microprocessor as before and used to control the position of the outer portion of the bellows end wall 36a. This process continues until the actual infusate flow rate equals the programmed one.

From that point on, the aforesaid process of adjusting the pressure in the reservoir 38, monitoring the control fluid pressure differential across restriction 64 and comparing the calculated actual flow rate to the desired one is repeated at appropriate sampling intervals as determined by the program in the microprocessor 84. The motor 78 is actuated only when the pressure differential deviates from a preset error limit programmed into the microprocessor.

The viscosity of the control fluid can be much higher than that of the infusate. Therefore, relatively large tubing can be used in the flow path 58 between the fluid pressure reservoirs 34 and 38. Accordingly, the flow rate of that fluid can be controlled very precisely over a wide range. This is seen from FIG. 5 which illustrates typical basal and bolus flow rate ranges for the apparatus 10 used to administer insulin.

Also, the control fluid may be selected to have a very low viscosity vs. temperature coefficient so that its flow characteristics do not change appreciably with changes in the patient's temperature. On the other hand, pressure changes to which the patient is subjected are reflected in a change in the pressure differential across the restriction 64 and therefore are compensated for by the microprocessor control of motor 78.

It is important to note that source 76 transmits force through an elastic member or spring comprising the resilient radially inner wall portion 36b of the bellows bottom wall 36a. The motor 78 is actuated only intermittently to store energy in that spring. The spring is flexed to whatever force level is required to establish the desired pressure differential across the restriction 64. By energizing the motor 78 only when necessary to maintain the same flexure of the spring, a constant force on the infusate bellows 32 is established which, in turn, results in a constant infusate pressure and flow rate to the patient. In other words, the motor 78 applies potential energy to the "spring" which is, in turn, transformed to substantially constant pressure work on the infusate.

In the case of insulin, the dosage schedule programmed into the microprocessor might call for a certain basal infusate flow rate for a twenty-four hour day. Then at certain times during the day, say, during the normal mealtime periods, a program may be externally initiated to call for that basal flow being supplemented by a higher bolus flow to compensate for the patient's increased glucose intake at those times. Accordingly, at the proper command for a bolus dose, the microprocessor 84 controls motor 78 so that the ring 110 applies increased force to the outer wall portion 36c of the bellows wall 36a for a selected period of time, e.g. one hour. That increased force increases the pressure of the control fluid in reservoir 38 thereby increasing the pressure differential across the flow restriction 64. That differential is sensed and compared with the bolus reference value programmed into the microprocessor. The position of the bellows wall portion 36c wall is then adjusted until the actual infusate flow value equals the reference value indicating a proper level of infusate flow for the bolus dose.

At the end of the prescribed one hour time period, the microprocessor 84 issues a command causing the motor 78 to rotate in reverse. The stepped ring 110 backs off to where it was originally, thereby relieving the force on the bellows wall portion 36c to restore the original pressure differential across restriction 64 set by the programmed microprocessor and which corresponds to the infusate basal flow rate. Even though the force on the bellows wall portion 36c is relieved as aforesaid, the control fluid pressure remains higher in reservoir 38 than in reservoir 34. Therefore, the check valve 72 between those two volumes remains closed.

When the supply of infusate in chamber 33 is depleted, the physician sends a telemetry signal to transceiver 92 informing it of this condition. The microprocessor 84 thereupon commands valve 52 to close and motor 78 to operate in reverse, thereby rotating the stepped ring 110 so as to permit bellows 36 to extend. The physician then inserts a hypodermic needle through the septum 22 so as to bottom on and close the valve member 54. Consequently, the fresh infusate is compelled to flow through tube 44 into chamber 33, causing bellows 32 to extend. Since the pressure in the displacement reservoir 34 is now higher than the pressure in pressure reservoir 38, the control fluid flows from reservoir 34 through tube 58 to reservoir 38 with the check valve 72 opening so as to shortcircuit the flow restriction 64. Therefore, the refilling of the apparatus can take place in a relatively short time. It is important to note also that during this refill cycle, the two closed valves 52 and 54 provide a redundant seal between the infusate chamber and the patient.

Thereupon, the hypodermic needle is withdrawn from chamber 42, permitting valve member 54 to open. The spring bias on the valve member 54 is designed for zero change in fluid volume inside the chamber 42 during valve closure while refilling the apparatus. The opening of member 54 relieves the pressure in chamber 33 to some extent, thereby dropping the pressure of the control fluid in reservoir 34 below the pressure in reservoir 38 so that the check valve 72 closes. The pump is now, in effect, "reprimed". The pressure sensor 66 resumes monitoring the pressure drop across the restriction 64 so that the motor 78, under the control of the microprocessor 84, i.e. applies the requisite constant force to the bellows end wall portion 36c to resume programmed infusate flow as described above.

As mentioned previously, an electrically operated valve 52 is included in the outlet tube 48 leading from chamber 33 to catheter 18. If the pressure differential across restriction 64 deviates from the desired value for a preset time interval as measured by the transducer 66, this is recognized by the microprocessor 84. The processor thereupon issues a command signal to close valve 52, thereby discontinuing infusate flow to the infusion site. Valve 52 can also be designed to have a manual actuation capability with the valve being closed by a subcutaneous button or by a magnet positioned outside the patient's body opposite the valve. See, for example, U.S. Pat. No. 4,193,297. Thus, even if there is a catastrophic failure of both the electronic and mechanical subsystems in the apparatus 10, the patient himself would still be able to discontinue manually the infusate flow to catheter 18.

It should be appreciated that during normal operation, the apparatus 10 does not maintain control over the infusate flow from chamber 33 directly. Therefore, the tubing and any valving leading from that chamber can be quite large and flow restrictions are not required. Therefore, the molecules of the infusate issuing from chamber 33 suffer minimal damage and the outlet path from that chamber tends not to become clogged by the infusate.

If at any time it is desired to change the dosage schedule for a particular patient, the microprocessor 84 can be reprogrammed by means of the telemetry transceiver 92. This simply involves transmitting coded data by means of a telemetry transmitter positioned outside the patient's body opposite the receiving antenna 94. Apparatus for transmitting telemetry data to a device implanted in the human body is well known, an example of same being disclosed in U.S. Pat. No. 4,077,405.

The transceiver 92 can also be used to transmit telemetry data acquired by the microprocessor 84 exteriorly of the body. That is, the state of the pump and its functions such as volume infused, basal and bolus flow rates, battery condition, etc. can be monitored by conventional means and that information stored in the processor's memory. Periodically, the processor may be instructed to send that information to the transceiver for transmission to an external receiver so that the data can be evaluated.

It will be seen from the foregoing, then, that the present apparatus obtains very accurate control over the flow of infusate to the patient which control is achieved at both ends of a very wide range. That flow is substantially independent of temperature changes to which the patient may be subjected. Also, the feedback loop in the apparatus compensates for most pressure changes. Once implanted in the patient, the apparatus can remain there for a prolonged period, on the order of three years or more, before its battery requires recharging or replacement. During that time, the apparatus can be refilled with infusate as necessary simply by injecting fresh infusate through the patient's skin directly into the apparatus.

The aforesaid attributes, in addition to the ability to program the patient's dosage schedule and to change that schedule by reprogramming when required, make the present apparatus very versatile and useful for patients requiring long-term infusion of medicants at different, very low and very precise flow rates.

It will thus be seen that the objects set forth above, among those made apparent from the preceding description, are efficiently attained. Also, since certain changes may be made in the above construction without departing from the scope of the invention. For example, the bellows capsule 32 can be positioned concentrically inside capsule 36, the two capsules having common opposite ends, one of which is fixed and the other of which is moved by means 76. The space inside capsule 32 is now the infusate chamber 33 and the space outside that capsule, but inside bellows 36, is now the pressure chamber 38. Restricted conduit 58 leads from that chamber to the displacement chamber 34 which is now a separate bellows capsule. The operation of this version is substantially the same as that of the one described above. Also, instead of employing the illustrated cam arrangement for shifting the reference position of the pressure chamber, a stepping motor or solenoid-actuated ratchet may be used for that purpose. Therefore, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A programmable implantable infusate pump comprising
   A. a housing;
   B. a variable volume infusate chamber in the housing;
   C. means for conducting infusate from said chamber to an infusion site outside the housing;
   D. a variable volume fluid pressure reservoir in the housing;
   E. a variable volume fluid displacement reservoir in the housing;
   F. a fluid path extending between the pressure reservoir and the displacement reservoir, said path defining a flow restriction, said reservoirs and said path arranged to be filled with a substantially incompressible control fluid;
   G. means for monitoring the fluid pressure differential across said restriction and producing indications in response thereto;
   H. means acting between a reference position and the pressure reservoir for applying a substantially constant force to the pressure reservoir tending to reduce its volume; and
   I. means responsive to said indications for intermittently shifting the reference position so as to maintain a selected infusate flow rate from said chamber.

2. The pump defined in claim 1 wherein said constant force-applying means comprise a flexible resilient member.

3. The pump defined in claim 2 wherein said member includes a spring.

4. The pump defined in claim 2 wherein the force-applying means comprise a flexible resilient wall portion of said pressure reservoir.

5. The pump defined in claim 1 wherein said control fluid has a higher viscosity than infusate introduced into said chamber.

6. The pump defined in claim 1 and further including a self-sealing penetrable septum mounted in the housing wall in fluid communication with the infusate chamber to permit said chamber to be refilled with infusate by percutaneous injection through the septum.

7. The pump defined in claim 6 and further including means for flowing control fluid from the displacement reservoir to the pressure reservoir so as to bypass said restriction when the fluid pressure in the displacement reservoir exceeds the fluid pressure in the pressure reservoir during refilling of the infusate chamber.

8. The pump defined in claim 7 wherein said flowing means include a nonreturn valve.

9. The pump defined in claim 7 and further including means for blocking flow of infusate through the conducting means during refilling of the infusate chamber.

10. The pump defined in claim 1 wherein the sensing means comprise a differential fluid pressure transducer.

11. The pump defined in claim 1 wherein the infusate chamber and pressure reservoir each comprise a metal bellows capsule.

12. The pump defined in claim 1 wherein the volumes of the infusate chamber and pressure reservoir both change in a reciprocal fashion with respect to the displacement reservoir.

13. The pump defined in claim 12 wherein the pressure reservoir is a substantially closed volume extending around the infusate chamber.

14. The pump defined in claim 12 wherein the displacement reservoir is a substantially closed volume extending around the infusate chamber.

15. The pump defined in claim 1 wherein
   A. the pressure reservoir is a metal bellows having a closed free end wall;
   B. the force applying means is a flexible resilient radially inner portion of the bellows end wall;
   C. a wall of the housing extends opposite said bellows end wall; and
   D. the shifting means comprise means for moving a radially outer portion of the bellows end wall relative to said housing wall.

16. The pump defined in claim 15 wherein the moving means comprises
   A. movable cam means positioned between the bellows wall outer portion and said housing wall; and
   B. a DC electric motor for moving the cam means relative to the said bellows and housing walls.

17. The pump defined in claim 16 and further including a battery connected electrically to said motor.

18. The pump defined in claim 1 wherein the shifting means comprise
   A. means for moving the constant force means in response to an error command; and
   B. a microprocessor
      (1) connected to sample said indications; and
      (2) programmed to compute from said indications the flow rate.

19. The pump defined in claim 18 and further including means in the housing for reprogramming the microprocessor.

20. The pump defined in claim 19 wherein the reprogramming means includes telemetry means connected electrically to the microprocessor.

21. The pump defined in claim 18 and further including valve means for preventing infusate flow from the chamber when the error command persists for a determined time interval.

22. The pump defined in claim 21 wherein the valve means is actuated externally magnetically.

23. The pump defined in claim 21 wherein the valve means is actuated by pressure on the skin under which the pump is implanted.

24. The pump defined in claim 18 wherein the microprocessor is programmed to change said programmed rate in accordance with a programmed schedule to vary the infusate flow rate from said chamber.

25. The pump defined in claim 18
   A. wherein the microprocessor includes a memory for storing a plurality of programmed flow rates; and
   B. further including means electrically connected to the microprocessor and actuatable from outside the housing for selecting among said programmed flow rates.

26. The pump defined in claim 25 wherein the selecting means comprises a switch actuatable from outside the housing by pressure on the skin under which the pump is implanted.

27. The pump defined in claim 1 and further including
   A. means for monitoring pump operation to develop operating data; and
   B. telemetry means for transmitting said data exteriorly of the body.

28. The pump defined in claim 1 and further including
   A. means for refilling the infusate chamber; and
   B. means for resetting said reference position when the infusate chamber is refilled so as to "reprime" the pump.

* * * * *